(12) United States Patent
Salg

(10) Patent No.: US 10,139,305 B2
(45) Date of Patent: Nov. 27, 2018

(54) APPARATUS AND METHOD FOR MAKING CANISTER AND FOR DETECTING LEAKS FOR QUALITY ASSURANCE

(71) Applicant: PBM Nutritionals, LLC, Charlottesville, VA (US)

(72) Inventor: George M. Salg, Enosburg Falls, VT (US)

(73) Assignee: PBM Nutritionals, LLC, Charlottesville, VA (US)

( * ) Notice: Subject to any disclaimer, the term of this patent is extended or adjusted under 35 U.S.C. 154(b) by 553 days.

(21) Appl. No.: 14/762,490

(22) PCT Filed: Jan. 23, 2014

(86) PCT No.: PCT/US2014/012764
§ 371 (c)(1),
(2) Date: Jul. 22, 2015

(87) PCT Pub. No.: WO2014/116838
PCT Pub. Date: Jul. 31, 2014

(65) Prior Publication Data
US 2015/0355048 A1   Dec. 10, 2015

Related U.S. Application Data

(60) Provisional application No. 61/849,305, filed on Jan. 24, 2013, provisional application No. 61/849,306, filed on Jan. 24, 2013.

(51) Int. Cl.
*A61L 2/10* (2006.01)
*G01M 3/32* (2006.01)
*B65B 55/08* (2006.01)

(52) U.S. Cl.
CPC .............. *G01M 3/329* (2013.01); *A61L 2/10* (2013.01); *B65B 55/08* (2013.01)

(58) Field of Classification Search
CPC ....... B65B 1/02; B65B 7/2807; B65B 7/2842; B65B 7/285; B65B 7/2857; B65B 25/001;
(Continued)

(56) References Cited

U.S. PATENT DOCUMENTS

D82,247 S    10/1930  Campbell
2,738,900 A   3/1956  Wenger
(Continued)

FOREIGN PATENT DOCUMENTS

CA    2781585 A1 *  6/2011    ........... B65D 43/162
CN    1303347 A     7/2001
(Continued)

*Primary Examiner* — Stephen F. Gerrity
(74) *Attorney, Agent, or Firm* — Breiner & Breiner, L.L.C.

(57) ABSTRACT

The invention is directed to a canister for packaging and delivering a product such as, but not limited to, infant formula. The canister of the invention includes a container and cover. The cover includes a base and a lid with the base including an easy-open sealing material and/or a utensil for dispensing the product and docking station for holding the utensil when not in use. This invention is further directed to an apparatus and method for the in-line sterilization of the cover during the manufacture thereof. The invention is further directed to an apparatus and method for the in-line detection of leaks in the canister for quality assurance.

14 Claims, 14 Drawing Sheets

(58) Field of Classification Search
CPC ..... B65B 31/022; B65B 31/025; B65B 55/08; G01M 3/226; G01M 3/227; G01M 3/229; G01M 3/32; G01M 3/3209; G01M 3/3236; G01M 3/3272; G01M 3/3281; G01M 3/329; B67B 3/003
USPC ................ 53/426, 471, 53, 167, 282, 284.5; 73/45.3, 49.3, 52; 250/455.11; 422/24
See application file for complete search history.

(56) References Cited

U.S. PATENT DOCUMENTS

| | | | |
|---|---|---|---|
| 3,448,888 A | 6/1969 | Smith et al. | |
| 3,722,779 A | 3/1973 | Chang | |
| 3,893,566 A | 7/1975 | Ross | |
| 3,955,742 A | 5/1976 | Marshall et al. | |
| D254,842 S | 4/1980 | Berner | |
| 4,211,336 A | 7/1980 | Helms | |
| 4,432,466 A | 2/1984 | Allen | |
| 4,453,646 A | 6/1984 | Harrild | |
| D280,704 S | 9/1985 | Dalton | |
| 4,715,215 A * | 12/1987 | Perhach et al. | G01M 3/363 73/49.3 |
| 4,724,977 A | 2/1988 | Cleevely et al. | |
| 4,844,263 A | 7/1989 | Hadtke | |
| 4,899,574 A | 2/1990 | Potteiger | |
| 4,922,746 A * | 5/1990 | Hulsman et al. | G01M 3/366 73/49.3 |
| D311,334 S | 10/1990 | Flynn et al. | |
| 4,966,301 A | 10/1990 | Yamashita et al. | |
| 5,009,310 A | 4/1991 | Finney | |
| 5,029,463 A * | 7/1991 | Schvester et al. | G01M 3/227 73/40.7 |
| 5,054,642 A | 10/1991 | Yoshida | |
| 5,090,572 A | 2/1992 | DeRoseau | |
| 5,125,528 A | 6/1992 | Heyn et al. | |
| 5,129,212 A * | 7/1992 | Duffey et al. | B65B 55/022 141/10 |
| 5,145,088 A | 9/1992 | Goujon | |
| 5,373,729 A * | 12/1994 | Seigeot | G01M 3/227 73/40.7 |
| 5,409,126 A | 4/1995 | DeMars | |
| 5,443,174 A | 8/1995 | Bauer | |
| 5,515,974 A | 5/1996 | Higson | |
| 5,705,212 A | 1/1998 | Atkinson | |
| 5,706,974 A | 1/1998 | Murdick et al. | |
| 5,775,531 A | 7/1998 | Lowry | |
| 5,865,335 A | 2/1999 | Farrell et al. | |
| 5,915,270 A * | 6/1999 | Lehmann | G01M 3/329 73/49.2 |
| 5,958,336 A | 9/1999 | Duarte | |
| 5,982,284 A | 11/1999 | Baldwin et al. | |
| 5,992,667 A | 11/1999 | Huang | |
| 6,064,306 A | 5/2000 | Deschenes et al. | |
| 6,105,419 A | 8/2000 | Michels et al. | |
| 6,153,287 A | 11/2000 | Gasnier | |
| D462,012 S | 8/2002 | Manderfield, Jr. | |
| D470,412 S | 2/2003 | Palmer-Ball | |
| D473,140 S | 4/2003 | Gilliam et al. | |
| D476,898 S | 7/2003 | Schuller et al. | |
| 6,591,981 B2 | 7/2003 | Draghetti | |
| 6,604,645 B1 | 8/2003 | Vaupotic | |
| D479,955 S | 9/2003 | Samartgis | |
| D483,988 S | 12/2003 | Kipperman et al. | |
| D484,797 S | 1/2004 | Kipperman et al. | |
| 6,710,357 B1 * | 3/2004 | Schweitzer | A61L 2/10 250/492.1 |
| 6,761,279 B1 | 7/2004 | Martin et al. | |
| 6,761,283 B1 | 7/2004 | Gilliam et al. | |
| 6,772,904 B1 | 8/2004 | Gilliam et al. | |
| D501,754 S | 2/2005 | Munson et al. | |
| 6,955,381 B2 | 10/2005 | Parker et al. | |
| 7,038,219 B2 * | 5/2006 | Clark et al. | B65B 55/16 250/455.11 |
| 7,040,500 B2 | 5/2006 | Kipperman et al. | |
| D528,919 S | 9/2006 | Kipperman et al. | |
| D530,616 S | 10/2006 | Kipperman et al. | |
| D530,617 S | 10/2006 | Little et al. | |
| D533,713 S | 12/2006 | Tucci et al. | |
| 7,175,041 B2 | 2/2007 | Ekkert | |
| D541,598 S | 5/2007 | Kim | |
| D541,648 S | 5/2007 | Bennett et al. | |
| D553,988 S | 10/2007 | Perry et al. | |
| D555,487 S | 11/2007 | Perry et al. | |
| D562,640 S | 2/2008 | Tucker et al. | |
| D562,680 S | 2/2008 | Vrhovski | |
| D566,482 S | 4/2008 | Tucker et al. | |
| 7,370,788 B1 | 5/2008 | Otani et al. | |
| D576,035 S | 9/2008 | Perry et al. | |
| D578,401 S | 10/2008 | Perry et al. | |
| 7,464,475 B2 | 12/2008 | Tsao | |
| D586,217 S | 2/2009 | Pedmo et al. | |
| 7,528,727 B2 | 5/2009 | Morrow | |
| D595,131 S | 6/2009 | Dibnah et al. | |
| D600,131 S | 9/2009 | Perry et al. | |
| 7,621,417 B2 | 11/2009 | Peterson et al. | |
| D605,041 S | 12/2009 | Perry et al. | |
| 7,631,776 B2 | 12/2009 | Vovan et al. | |
| D624,406 S | 9/2010 | Cronican et al. | |
| D628,062 S | 11/2010 | Snedden et al. | |
| 7,878,352 B2 | 2/2011 | von Spreckelsen et al. | |
| D640,544 S | 6/2011 | Sifuentes et al. | |
| 7,963,421 B2 | 6/2011 | Zeiler et al. | |
| 7,967,167 B2 | 6/2011 | Tilton | |
| 7,971,747 B2 | 7/2011 | Blomdahl et al. | |
| D646,923 S | 10/2011 | Chhay | |
| 8,042,704 B2 | 10/2011 | Borowski et al. | |
| D648,171 S | 11/2011 | Rusnak | |
| D666,876 S | 9/2012 | Rusnak | |
| D675,477 S | 2/2013 | McGrath, Jr. et al. | |
| D676,739 S | 2/2013 | McGrath, Jr. et al. | |
| 8,376,179 B2 | 2/2013 | Horton et al. | |
| D677,164 S | 3/2013 | Jones et al. | |
| 8,469,223 B2 | 6/2013 | Perry et al. | |
| 8,770,423 B2 | 7/2014 | McGeough | |
| D715,148 S | 10/2014 | Kuo et al. | |
| D723,920 S | 3/2015 | Wakeham et al. | |
| 2001/0035424 A1 | 11/2001 | Combe et al. | |
| 2006/0125642 A1 | 6/2006 | Chandaria | |
| 2006/0156811 A1 | 7/2006 | Borowski et al. | |
| 2006/0207963 A1 | 9/2006 | Little et al. | |
| 2006/0220868 A1 | 10/2006 | Takasawa et al. | |
| 2006/0230826 A1 | 10/2006 | Nakamura et al. | |
| 2006/0255052 A1 | 11/2006 | Svitak | |
| 2006/0289376 A1 | 12/2006 | Von Spreckelsen et al. | |
| 2008/0041861 A1 | 2/2008 | Crawford et al. | |
| 2008/0156805 A1 | 7/2008 | Perry et al. | |
| 2008/0156806 A1 | 7/2008 | Perry et al. | |
| 2008/0156808 A1 | 7/2008 | Perry et al. | |
| 2008/0156858 A1 | 7/2008 | Perry et al. | |
| 2008/0173657 A1 | 7/2008 | Perry et al. | |
| 2008/0186367 A1 | 8/2008 | Adkins et al. | |
| 2008/0284567 A1 | 11/2008 | Portier et al. | |
| 2009/0184120 A1 | 7/2009 | Stevens | |
| 2009/0308139 A1 | 12/2009 | Fox | |
| 2010/0031747 A1 | 2/2010 | Hall | |
| 2010/0051631 A1 | 3/2010 | Blomdahl et al. | |
| 2010/0108670 A1 | 5/2010 | Perry et al. | |
| 2010/0108673 A1 | 5/2010 | Kurosawa et al. | |
| 2010/0206751 A1 | 8/2010 | Wessel | |
| 2010/0213095 A1 | 8/2010 | Eiten | |
| 2010/0242411 A1 | 9/2010 | Boekstegers et al. | |
| 2010/0270323 A1 | 10/2010 | Zeiler et al. | |
| 2010/0308044 A1 | 12/2010 | Perry et al. | |
| 2010/0308052 A1 | 12/2010 | Zeiler et al. | |
| 2010/0308065 A1 | 12/2010 | Vandamme et al. | |
| 2010/0308066 A1 | 12/2010 | Perry et al. | |
| 2011/0006066 A1 | 1/2011 | Vandamme et al. | |
| 2011/0139783 A1 | 6/2011 | Fisher | |
| 2011/0174817 A1 | 7/2011 | Blomdahl et al. | |
| 2011/0186570 A1 | 8/2011 | Perry et al. | |
| 2012/0134878 A1 * | 5/2012 | Silvestri | B67B 3/003 422/22 |

(56) References Cited

U.S. PATENT DOCUMENTS

| | | | |
|---|---|---|---|
| 2012/0141322 A1* | 6/2012 | Fogg | A61L 9/20 422/24 |
| 2012/0279964 A1 | 11/2012 | McGeough | |
| 2013/0272920 A1* | 10/2013 | Knott et al. | B67B 3/003 422/22 |
| 2014/0097183 A1 | 4/2014 | McGrath et al. | |

FOREIGN PATENT DOCUMENTS

| | | | | |
|---|---|---|---|---|
| CN | 1504392 A | | 6/2004 | |
| CN | 1696022 A | | 11/2005 | |
| DE | 10252499 A1 | | 5/2004 | |
| FR | 2915969 A1 | | 11/2008 | |
| GB | 766190 A | * | 1/1957 | A61L 2/10 |
| GB | 1217457 A | * | 12/1970 | G01M 3/229 |
| GB | 2086834 A | * | 5/1982 | B65D 31/025 |
| GB | 2222687 A | * | 3/1990 | G01M 3/329 |
| GB | 2250271 A | | 6/1992 | |
| GB | 2381785 A | | 5/2003 | |
| GB | 2384478 A | * | 7/2003 | B65B 7/285 |
| GB | 2424863 A | | 10/2006 | |
| JP | H07094251 B2 | * | 10/1995 | A61L 2/10 |
| JP | 2002128030 A | * | 5/2002 | B67B 3/003 |
| JP | 2007099287 A | | 4/2009 | |
| WO | 9961336 A1 | | 12/1999 | |
| WO | 9961337 A2 | | 12/1999 | |
| WO | WO 0109583 A1 | * | 2/2001 | G01M 3/329 |
| WO | 2005016779 A1 | | 2/2005 | |
| WO | 2005075314 A2 | | 8/2005 | |
| WO | 2007109891 A1 | | 10/2007 | |
| WO | 2008083141 A2 | | 7/2008 | |
| WO | 2010027398 A1 | | 3/2010 | |
| WO | 2011067585 A1 | | 6/2011 | |
| WO | 2011081677 A1 | | 7/2011 | |
| WO | 2011127133 A2 | | 10/2011 | |

* cited by examiner

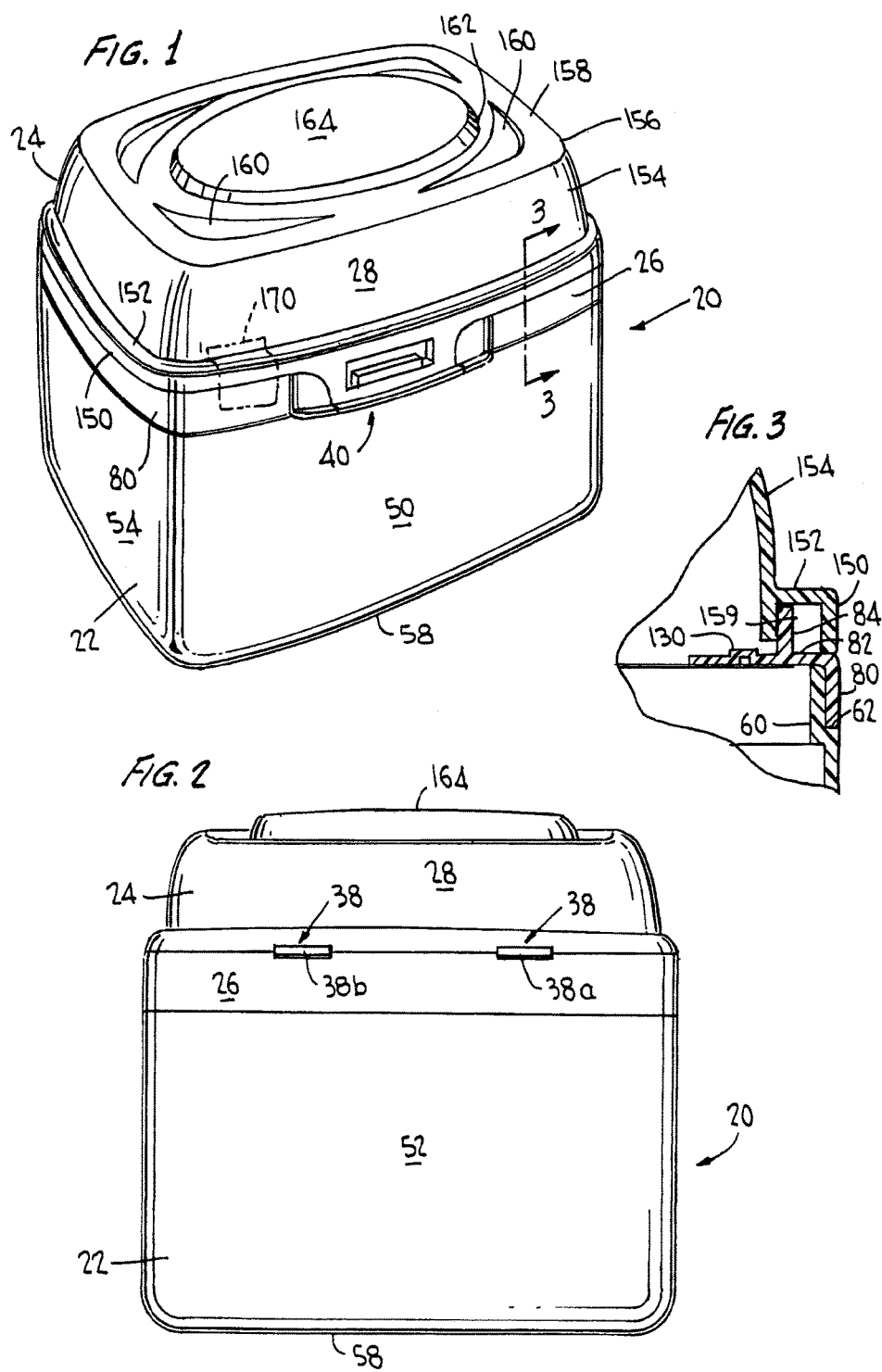

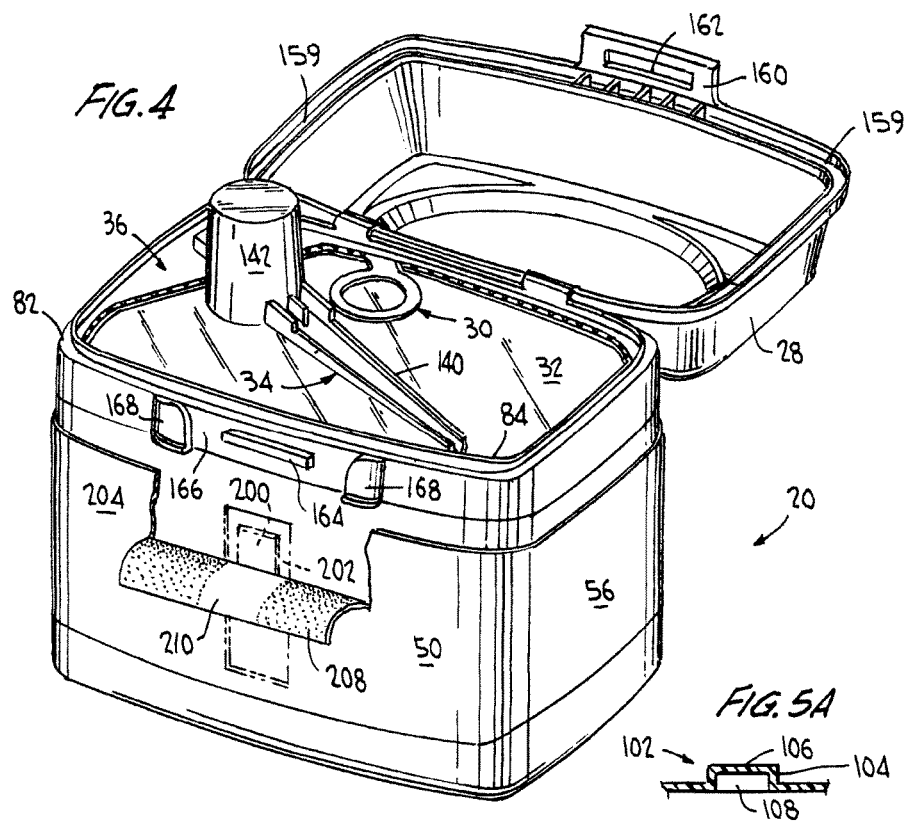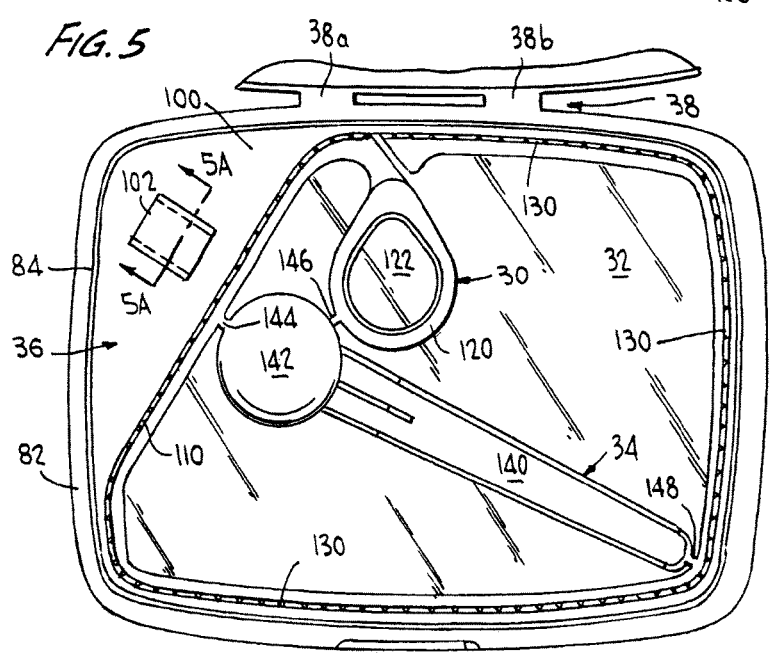

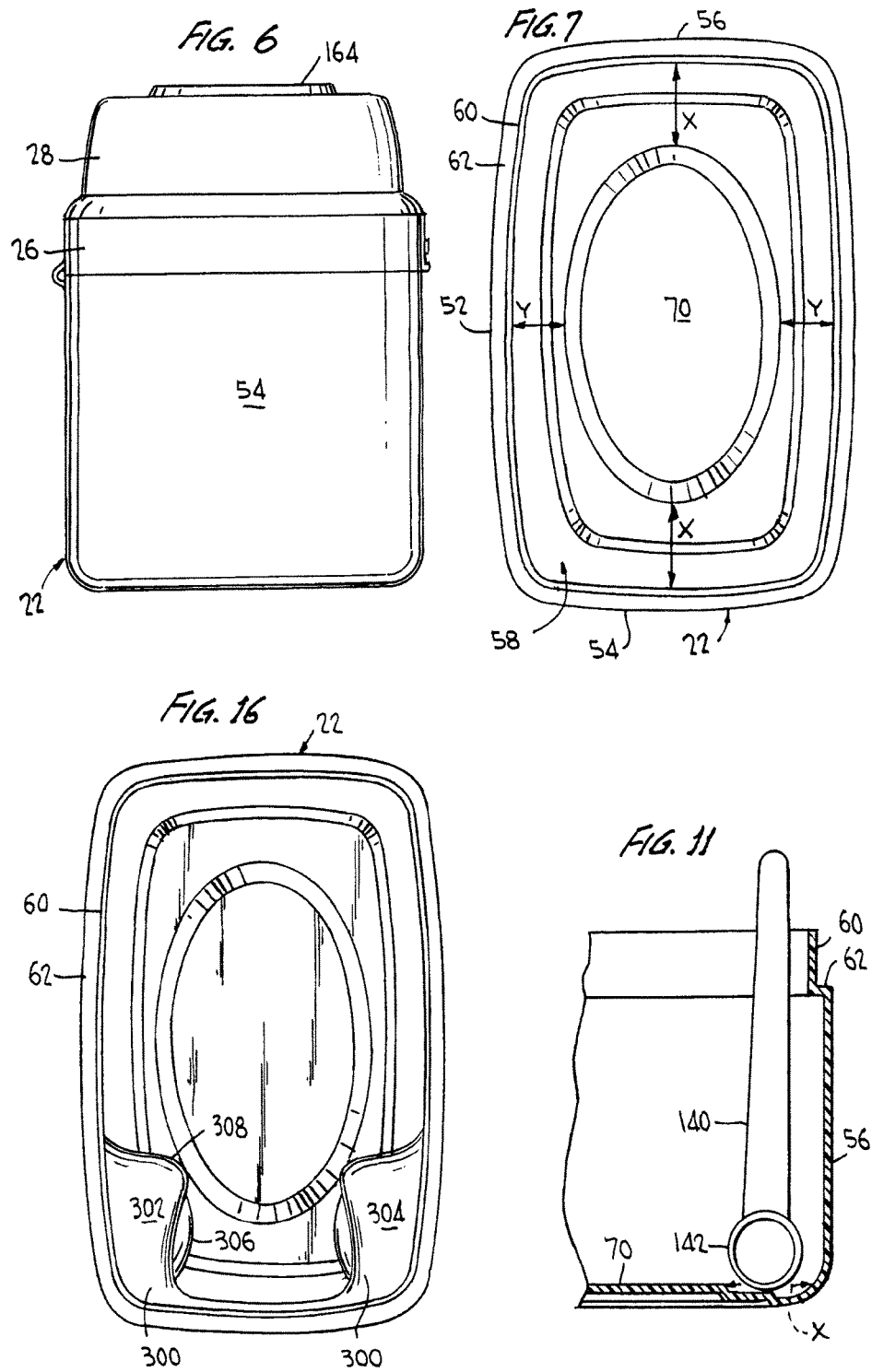

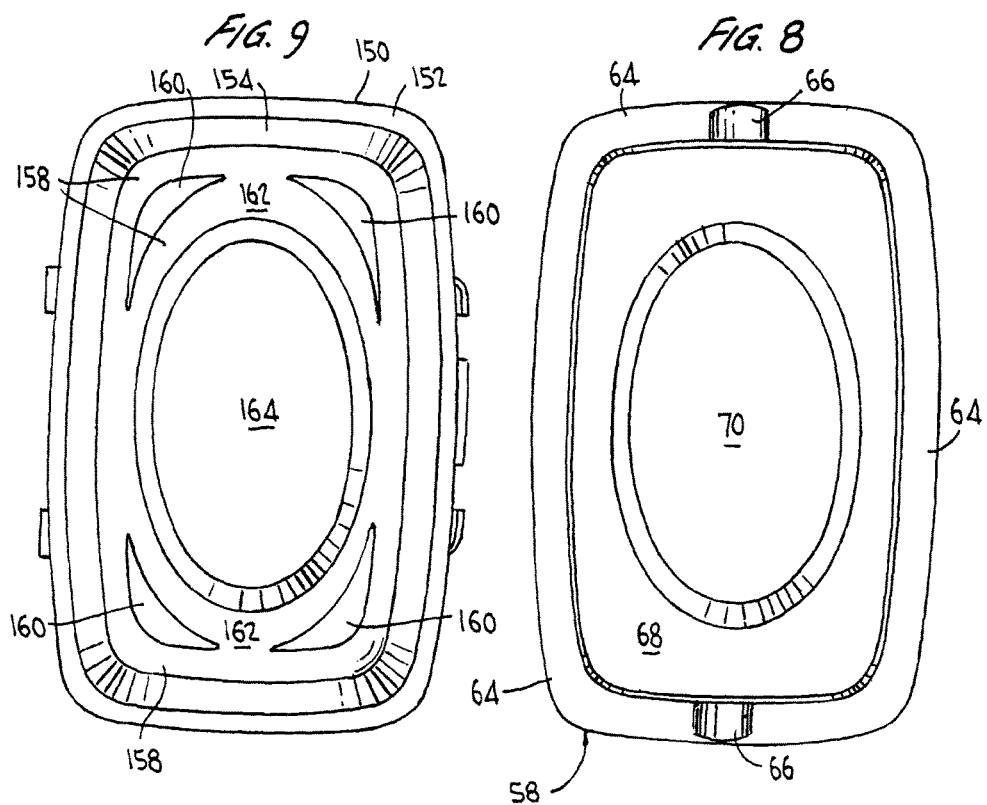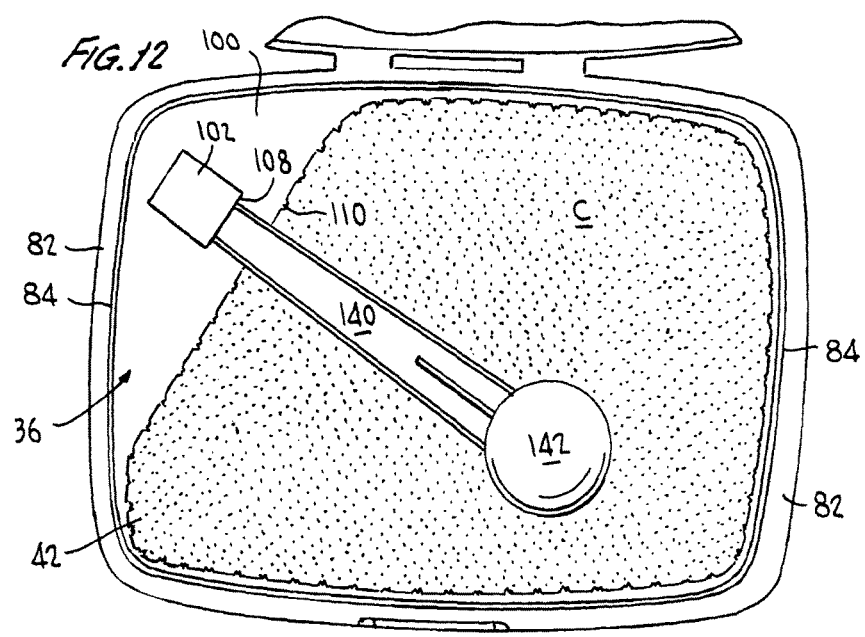

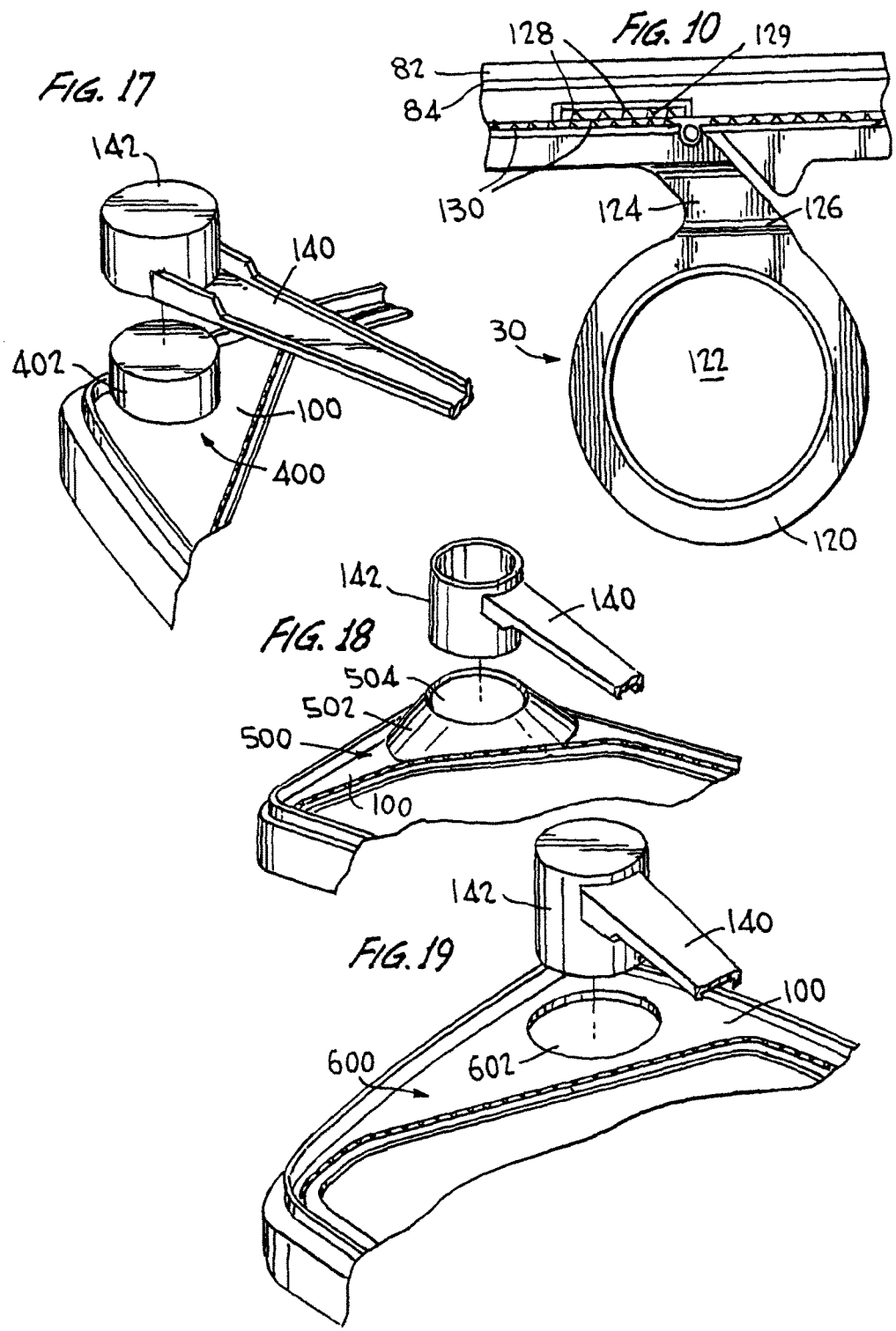

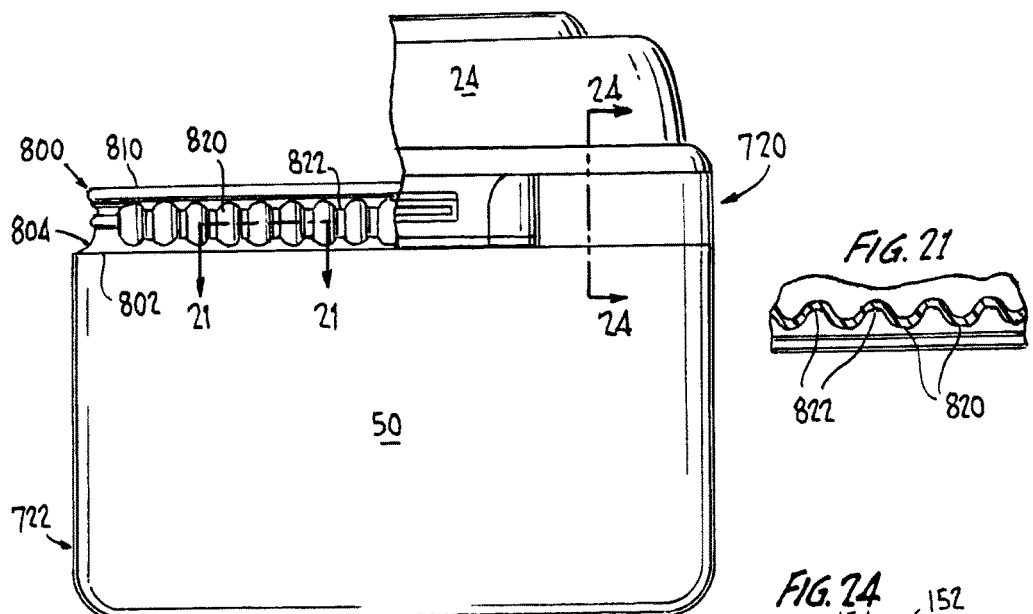
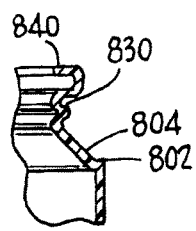
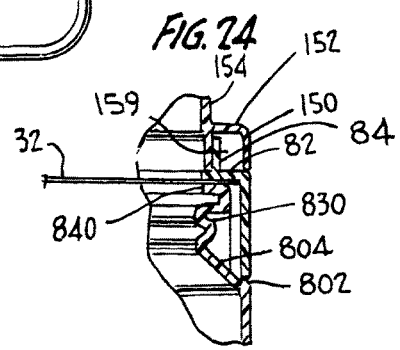
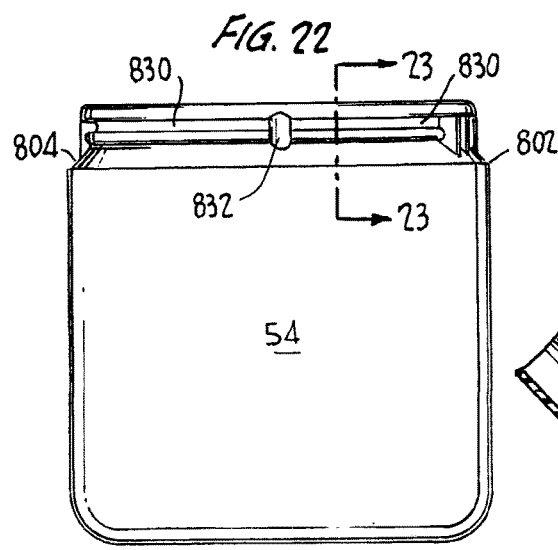
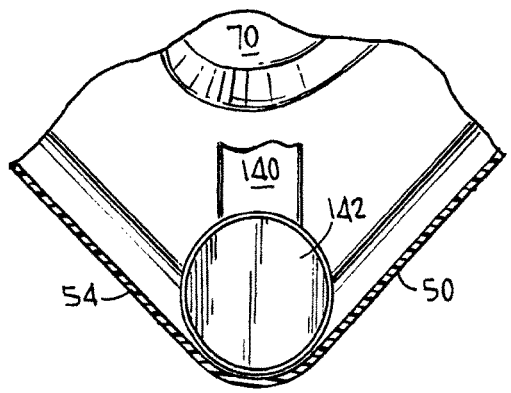

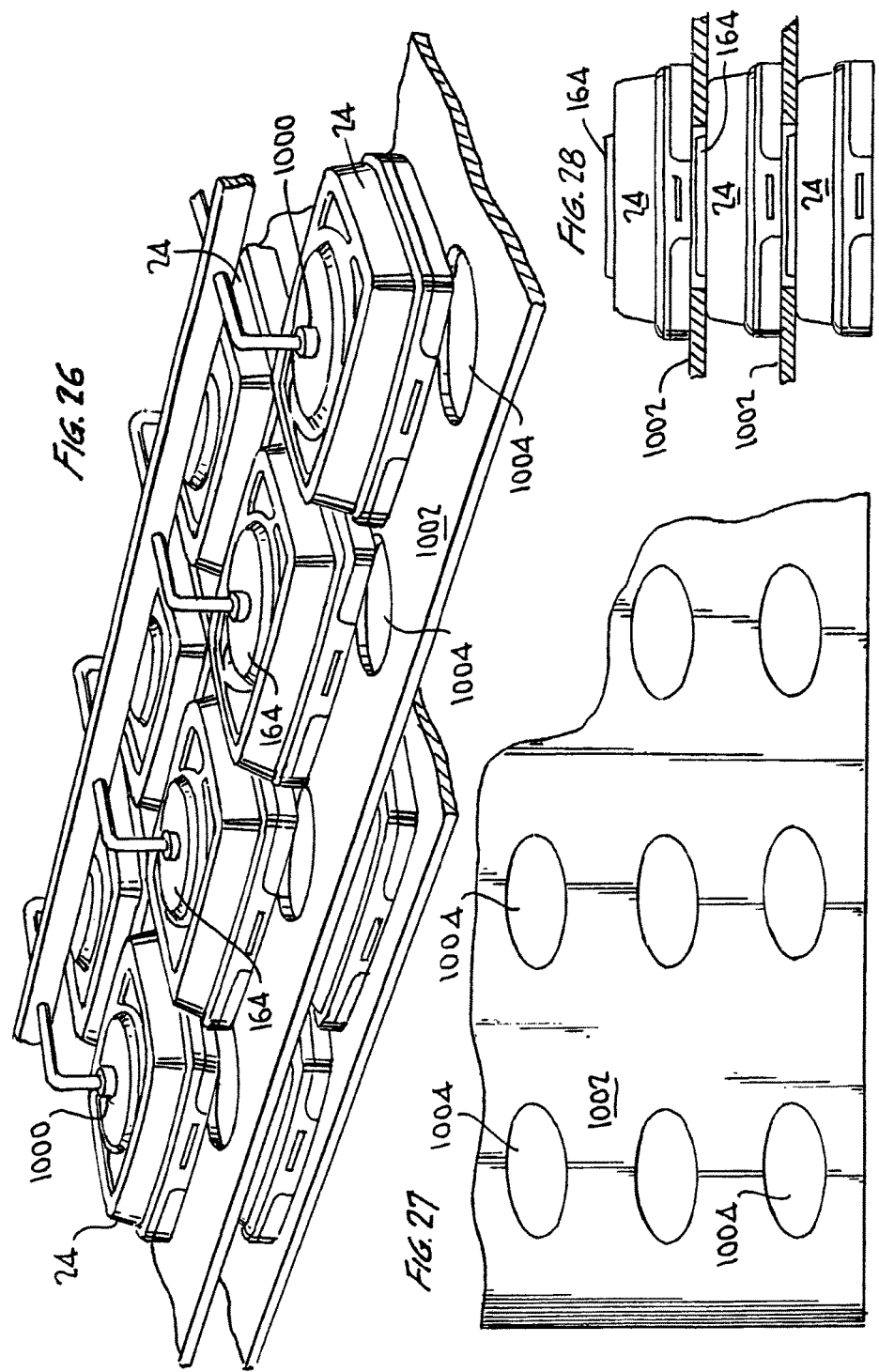

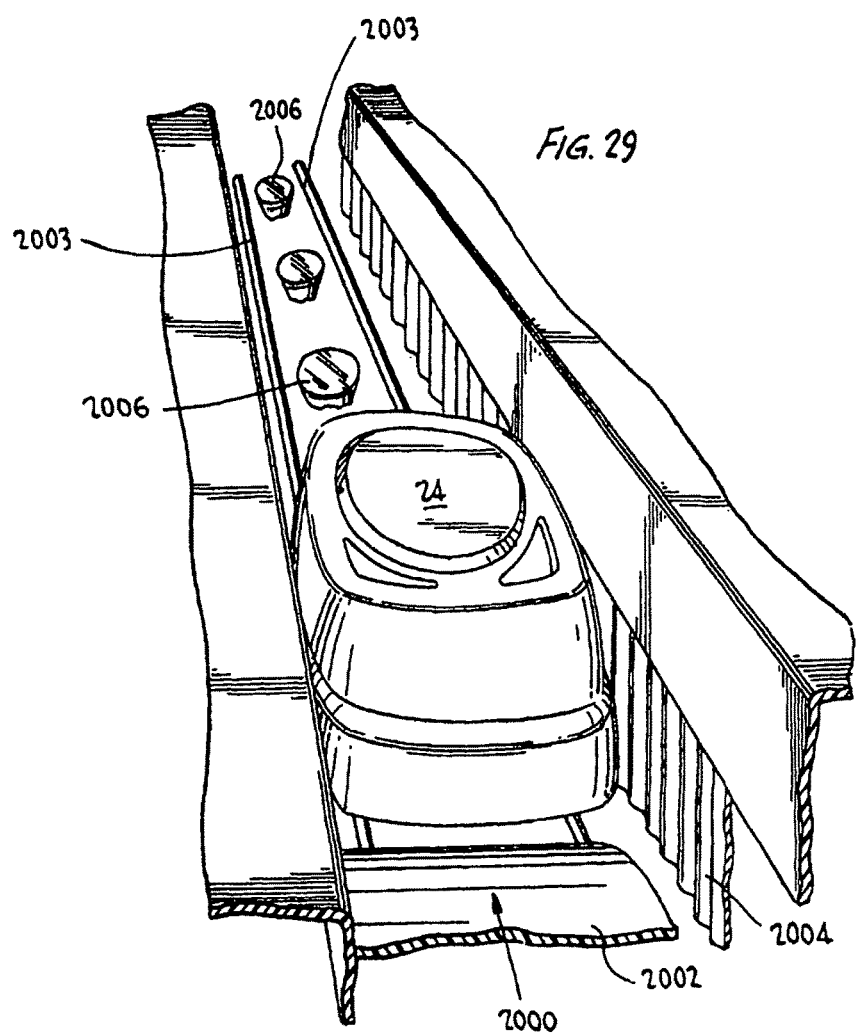

APPARATUS AND METHOD FOR MAKING CANISTER AND FOR DETECTING LEAKS FOR QUALITY ASSURANCE

RELATED APPLICATIONS

This application claims benefit of U.S. provisional application Ser. No. 61/849,306, filed Jan. 24, 2013, entitled "Canister And Method Of Making," and U.S. provisional application Ser. No. 61/849,305, filed Jan. 24, 2013, entitled "Canister And Apparatus And Method For Detecting Leaks For Quality Assurance," which applications are incorporated herein by reference in their entirety.

FIELD OF THE INVENTION

The present invention relates to an apparatus and method for making canisters for packaging and dispensing product such as, but not limited to, infant formula. More particularly, the invention is directed to a canister having a container and a cover wherein the cover includes a base and a lid and the base may include an easy-open sealing material and/or a utensil for dispensing the product and a docking station for receiving the utensil. The invention is directed to an apparatus and method for the sterilization of the cover during the manufacture thereof and to an apparatus and method for the in-line detection of leaks in the canister for quality assurance.

BACKGROUND OF THE INVENTION

Canisters are known in the art for packaging and dispensing of products, including powder materials such as infant formula. While the present invention is broader than the packaging and delivery of infant formula, the invention will be described in relation to infant formula with the understanding that the invention is not so limited.

Canisters for infant formula should include one or more means to indicate whether the canister has been tampered with. For example, many canisters utilize a seal between the lid and the container which, if broken, indicates that that canister may have been tampered with.

In packaging and dispensing infant formula, it is important that the infant formula be sealed in the container by a sealing material prior to opening and use. For example, foil materials have been used to seal the container to retain the infant formula in the canister and also to indicate that the infant formula has not been tampered with. Such sealable materials must be (1) easy to open and prevent spillage of the infant formula when opening the canister; and (2) not subject to the foil tearing during manufacturing process or during transport to the store.

Once the infant formula canister has been opened, it is desirable that the infant formula is easily dispensed from the canister. In dispensing the infant formula, it is preferable that there is no spillage of the infant formula due to the waste of the formula and the mess that it may create. Additionally, infant formula must be dispensed in specific amounts for mixing with water in a bottle for the feeding of a baby.

In dispensing infant formula, it is known to use a utensil having a handle and a scoop to dispense an appropriate amount of the infant formula. It is also known to include and store such utensils in the infant formula canister. For example, some utensils are stored in the infant formula requiring the user to place their hand in the infant formula to remove the utensil, thereby possibly contaminating the infant formula and getting formula on the hands of the user.

To alleviate this problem, it has been proposed to store the utensil in the lid of the canister. However, many of these utensils and their storage means have shortcomings such as (1) the utensils are limited in size and shape due to the storage means in the canister; (2) the utensils are difficult to remove after opening the canister; (3) the utensils are difficult to store after the canister has been opened; and (4) the utensils are difficult to remove from the storage structure.

Additionally, once the infant formula has been dispensed, it is desirable to store the utensil in the canister. As noted above, it is known to store utensils in the lid of the canister. However, such storage mechanisms, often including a bracket, may be difficult to manufacture and/or use by the consumer. For example, some utensils are stored in the lid of the canister by brackets making it difficult to place the utensil in the lid or remove the utensil from the lid, sometimes causing the canister to tip and spill formula.

It is also desirable that the infant formula canister not be constructed in such a manner as to allow the infant formula to become trapped in a gasket used to seal the container portion of the canister with the cover portion of the canister. This causes difficulty in closing the canister and spillage of the infant formula.

With known canisters, the utensil is limited in its length due to the size of the container lid in which it is stored. This may require a user to place their hand into the container body when removing infant formula. In some instances, the infant formula will come in contact with the user's hand thereby possibly contaminating the infant formula and making dispensing difficult and messy.

Known canisters also may not withstand substantial pressure. For example, when pressure is applied to the top of certain known canisters, the canisters may fail, including causing the foil material to burst or tear; causing the cover to separate from the base of the canister or the like. Additionally, when canisters are transported at different elevations, there is the possibility that an increase in pressure may cause the canister to fail, including bursting of the canister or failure of the foil material sealed to the container rim.

Although known canisters have been provided to package and dispense infant formula, there are disadvantages to the canisters on the market, some of which have been noted above. Accordingly, there is a need in the market for an improved canister for packaging and dispensing infant formula or other material and an apparatus and method for making the canister.

SUMMARY OF THE INVENTION

The present invention is directed to a canister comprising a container and a cover attached to the container. The cover includes a base and a lid. The base further includes a docking station for removably holding a utensil. The docking station may include different configurations. One configuration may include a member extending from an edge on the base and having a storage structure for holding the utensil.

The present invention is further directed to a canister comprising a container and a cover attached to the container. The cover includes a base and a lid. The base may further include a docking station for removably holding a utensil. The base of the cover further includes an opening for dispensing a material in the container when the lid is in the open position. The base of the cover initially includes a sealable material to enclose the material in the canister. The sealable material may be removed by a removable closure mechanism which may comprise a ring tab. The ring tab includes a finger member and may have teeth at the end thereof for initially cutting into the sealing material to open the sealing material. Around the periphery of the base are perforations for the ring tab to follow when removing the sealable material.

The present invention is further directed to a canister comprising a container and a cover; the cover including a base and a lid; and the base further including a docking station for removably holding a utensil. The base further includes a utensil initially connected to the base by frangible members. When the canister is to be used, the lid is opened and the utensil may be removed from the base by breaking the frangible connections. The utensil may then be used to dispense material from the canister. When the utensil is not in use, it may be stored in the docking station.

The present invention is further directed to a canister comprising a container and a cover attached to the container, wherein the cover includes a base and a lid. The base further includes an opening for dispensing a material in the container when the lid is in the open position. The base of the cover initially includes a sealable material to enclose the material in the canister. The sealable material may be first attached to the underside of the base. The cover may then be attached to the canister container by induction sealing. The container may include reinforcing ribs and grooves at the rim of the container to add rigidity and strength to the container during the manufacturing process and to the finished container.

The canister is constructed and arranged to withstand substantial pressure during the manufacturing process, e.g. at least 40 psi. The completed canister will also withstand substantial vacuum pressure providing for a more durable canister, including during transport.

The present invention is further directed to a canister comprising a container and a cover attached to the container, wherein the cover includes a base and a lid. The base further includes a docking station for removably holding a utensil, and the container includes a gripping means for gripping the container.

The present invention is further directed to the sterilization of the cover during the in-line manufacture of the canister for quality assurance. More specifically, when assembling the canister for infant formula or other food product, the underside of the canister cover having the foil material adjacent to the infant formula or other food material should be sterile to prevent contamination and for quality assurance. The invention includes an apparatus and method for sterilization of the underside of the canister cover.

The present invention is further directed to an apparatus and method for the in-line detection of leaks in the canister for quality assurance. More specifically, once the canister has been filled with infant formula, each canister is vacuum checked during the in-line manufacturing process for leaks in the canister. If a leak is detected, the canister is removed from the production line. This assures quality of the product, including the prescribed shelf life of the product.

These and other embodiments of the invention will be apparent from the following description of the preferred embodiments of the invention and from the accompanying drawings.

BRIEF DESCRIPTION OF THE DRAWINGS

The following detailed description of specific non-limiting embodiments of the present invention can be best understood when read in conjunction with the following drawings, where like structures are indicated with like reference numbers.

FIG. 1 is a front perspective view of a canister of the present invention.

FIG. 2 is a back elevational view of the canister of FIG. 1.

FIG. 3 is a partial cross-sectional view of the container and cover of the canister taken along line 3-3 of FIG. 1.

FIG. 4 is a front perspective view of the canister of FIG. 1 with the cover in the open position.

FIG. 5 is a partial top view of the canister of FIG. 1 in an open position.

FIG. 5A is a cross-sectional view taken along line 5A-5A of FIG. 5.

FIG. 6 is a side elevational view of the canister of FIG. 1.

FIG. 7 is a top view of the interior of the container of the canister of FIG. 1.

FIG. 8 is a bottom view of the exterior of the canister of FIG. 1.

FIG. 9 is a top view of the canister of FIG. 1.

FIG. 10 is an enlarged partial top view of the mechanism for opening the canister of FIG. 1.

FIG. 11 is a partial cross-sectional view showing a utensil in the container of the canister.

FIG. 12 is a partial top view of the canister of FIG. 1 in the open position showing the utensil in the docking station.

FIG. 16 is a top view of the interior of the container of the canister of FIG. 13.

FIG. 17 is an alternative embodiment of a docking station to be used in the canister of the invention.

FIG. 18 is an alternative embodiment of a docking station to be used in the canister of the invention.

FIG. 19 is an alternative embodiment of a docking station to be used in the canister of the invention.

FIG. 20 is a partial front view of another embodiment of the canister invention.

FIG. 21 is a partial cross-section taken along lines 21-21 of FIG. 20.

FIG. 22 is a side view of the container of the canister of FIG. 20.

FIG. 23 is a partial cross-section taken along lines 23-23 of FIG. 22.

FIG. 24 is a partial cross-sectional view of the container and cover of the canister of FIG. 20 taken along lines 24-24 of FIG. 20.

FIG. 25 is a partial view of the container of the invention illustrating the scoop fitting within a corner of the container.

FIG. 26 is a partial view showing a pallet carrying a plurality of covers of the invention during the manufacturing process and including a slip sheet between the covers.

FIG. 27 is a partial view showing the slip sheet separating the covers as shown in FIG. 26.

FIG. 28 is a partial elevational view of the plurality of covers of FIG. 26.

FIG. 29 is a partial perspective view of the in-line manufacture of the canister showing the sterilization tunnel for the sterilization of the canister cover.

DETAILED DESCRIPTION OF THE PREFERRED EMBODIMENTS

Preferred embodiments of the canister invention are illustrated in FIGS. 1-28. It is understood that the invention is not limited to these preferred embodiments. One primary useful function of the canister invention is for packaging and dispensing infant formula. The invention will, therefore, be illustrated with reference to packaging and dispensing infant formula. However, it is understood by those skilled in the art that the invention is not so limited and that other materials may be packaged and dispensed from the canister of the invention including, for example, other powder or pulverized materials such as coffee, cereal, etc.

Figure 13:
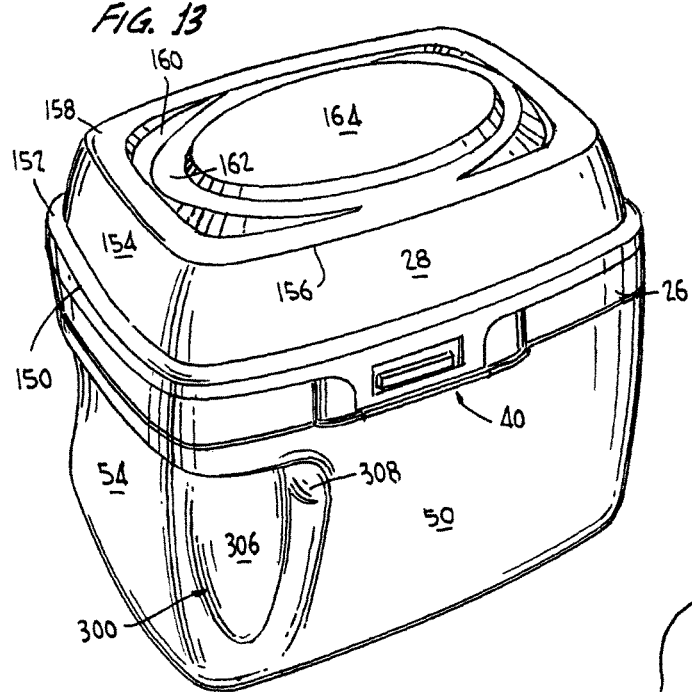
FIG. 13 is a front perspective view of another embodiment of the canister invention.

The canister of the invention as illustrated, for example, in FIGS. 1, 13 and 20 show preferred embodiments having a generally rectangular configuration. Again, it will be understood by those skilled in the art that other shaped canisters may be useful without departing from the scope of the invention, including square, round or other shaped canisters. Similarly, in the preferred embodiments, the canister is made of plastic such as polyethylene and polypropylene or a combination of materials. As discussed hereafter, the canister of the invention includes two primary components namely, the container for packaging the infant formula or other material and the cover portion which includes a base and a lid. The canister is preferably made by molding the container as one component and molding the cover (with the utensil) as another component. However, other methods known to those skilled in the art may be used.

FIGS. 1-12 illustrate a first preferred embodiment of the canister invention. FIGS. 13-16 illustrate a second embodiment of the canister invention. As seen hereafter, the primary difference between these two embodiments is that the second embodiment shown in FIGS. 13-16 includes gripping means for gripping the container of the canister. FIGS. 17-19 illustrate alternative embodiments of the docking station. FIGS. 20-24 illustrate a third embodiment of the canister invention. As seen hereafter, the primary difference between the first embodiment in FIGS. 1-12 and the third embodiment in FIGS. 20-24 is directed to the container and the means for attaching the cover to the container. FIG. 25 illustrates the scoop fitting within a corner of the container of the canister. FIGS. 26-28 illustrate the method of transporting the canister covers prior to manufacturing the canister. FIG. 29 illustrates the apparatus and method for the in-line manufacture of the canister including the sterilization of the canister cover. FIGS. 30-33 illustrate an apparatus and method for in-line detection of leaks in the canister for quality assurance.

We will hereafter describe the primary aspects of the canister invention and then illustrate the operation of a preferred embodiment of the invention. Specifically, referring to FIGS. 1-6 it will be seen that the first embodiment of the invention includes a canister 20. The canister 20 includes a container 22 and a cover 24. The cover 24 includes a base 26 and a lid 28. The base 26 includes a ring tab mechanism 30 for opening the canister to expose the stored contents C (FIG. 12). The contents are stored and secured in the canister 20 by a sealing material 32. The base 26 further includes a utensil 34 and a docking station 36 for receiving utensil 34 when the utensil is not in use. The lid 28 is connected to the base 26 by a hinge 38. The canister is closed by a latch 40. The specific components of the canister will now be discussed in further detail.

The container 22 includes a front 50, back 52, sides 54 and 56, bottom 58 and rim 60. Rim 60 includes a shoulder portion 62. Referring to FIG. 8, the exterior of the bottom 58 includes a base 64 for engaging a surface such as a store shelf or kitchen counter and having grooves 66 therein. There is a first recessed area 68 and a second deeper recessed area 70 for engaging the top of lid 28 for stacking of multiple canisters as discussed hereafter. Referring to FIG. 7, the interior surface of the bottom 58 has a dimension "X" between side walls 54 and 56 and recess 70 of a size sufficient to receive the scoop portion of utensil 34 for removing remaining amounts of infant formula when the formula is close to depletion as shown in FIG. 11. The area "Y" between recess 70 and front wall 50 and rear wall 52 has a smaller dimension and is not sized to receive the scoop portion of utensil 34. Accordingly, the canister may be tipped at one end to remove any remaining contents of stored material in the region generally designated "X." However, as seen in FIGS. 7, 8 and 11, there are two separate channel areas formed by recesses 68 and 70 and the scoop portion of the utensil 34 does not fit flushly in these channel areas. Therefore, as discussed hereafter with reference to FIG. 25, the utensil scoop is designed to fit into the corner area and the junction of the front, back and side walls to most easily remove the last amounts of infant formula.

The cover 24 includes base 26 and lid 28, preferably made of the same material and molded as a single unit by, for example, injection molding. Base 26 and lid 28 are joined by a hinge 38. Hinge 38 is preferably a living hinge having two members 38a and 38b, although a single member or multiple members may be used. It is further understood that other hinge mechanisms as known to those skilled in the art may be used without departing from the scope of the invention, e.g. pin and socket hinges.

Referring to FIG. 3, base 26 further includes a vertical wall 80. Adjacent wall 80 is a ledge 82 joined to a vertical wall 84 which extends around the periphery of base 26 and for receiving lid 28 and providing a sealed closure as discussed hereafter. Wall 80 engages rim 60 of container 22 by friction fit. This allows the cover 24 to be attached to the container 22. Container 22 and cover 24 may be attached to one another by other means as known to those skilled in the art.

Base 26 further includes a docking station 36. Referring to FIGS. 5 and 5A, in a presently preferred embodiment, the docking station includes a generally triangular portion 100 (although other configurations may be used) having a storage structure 102 for receiving and removably holding utensil 34. Storage structure 102 includes an inverted U-shaped member having legs 104 and top portion 106 providing a slot 108 for receiving the handle end of utensil 34. As shown for example in FIG. 12, the handle end of the utensil may be inserted into the slot 108 of U-shaped member for holding the utensil when not in use. The utensil may be placed in the docking station 36 with the scoop portion facing either up into the lid portion of the cover 24 as shown in FIG. 12 or down into the container portion of the canister (not shown). It is understood that when the package is first opened that the scoop portion will usually need to face up into the lid portion as the utensil scoop may not easily fit into a full container of infant formula or other material. Additionally, slot 108 may be modified such that the utensil may be held with the scoop facing sideways. Triangular portion 100 includes edge 110 which may be used to level the amount of infant formula or other material in utensil 34.

Referring to FIGS. 4, 5, 10 and 12, the base 26 further includes a ring tab mechanism 30 for opening the canister to expose the infant formula for dispensing. The infant formula is sealed in the canister by a sealing material 32 such as a foil sealant as described hereafter. The ring tab 30 includes a ring 120 with an opening 122 for engaging the user's finger to apply upward force to lift the tab to remove the sealing material 32 to expose the infant formula or other material C at opening 42 as shown in FIG. 12. The tab 120 includes a finger portion 124 joined to the tab 120 at a junction 126. The finger 124 extends downwardly toward the base of wall 84 at about a 45 degree angle. Referring to FIG. 10, at the end of finger 124 are one or more teeth 128 having a sharp edge 129 to tear sealant material 32 to begin the removal of the material 32 as described hereafter. In this embodiment, five teeth members 128 are used, although another number of teeth may be used or no teeth members need to be used without departing from the scope of the invention. Extending around an inside periphery of the base 26 and in conjunction with ring tab 120 are perforations 130 (in the plastic material) adjacent wall 84 and edge 110 and attached to the sealing material 32, a preferred material being a foil material. The foil 32 is sealed to the underside of the base 26 by induction welding, an adhesive or the like.

While the preferred embodiment discloses and uses a single ring tab 30, an alternate embodiment of the invention may use two ring tab members 30. For example, a first ring tab 30 may be adjacent to a second ring tab member 30, whereby the first ring tab is pulled to the left and the second ring tab is pulled to the right. This may allow for greater ease in opening the container. Additionally, a single ring tab may be used which may be constructed and arranged so that when pulled up the perforation will break in both directions and meet at the opposite side to remove the ring tab and foil.

The base 26 further includes a utensil 34. Utensil 34 includes a handle portion 140 and scoop portion 142. Referring to FIG. 5, the utensil 34 is initially attached to the base frangible members 144, 146 and 148 to hold the utensil in place before use, although a different number of frangible members may be used. The utensil 34 and frangible members are formed as part of the molding process when making cover 24. The utensil is preferably placed at a diagonal as shown in FIGS. 4 and 5 and which allows for a longer handle 140 which may extend outside of the container 22 when in use as shown in FIG. 11. This will allow the user of the utensil to scoop out infant formula without touching the infant formula, thereby precluding the possible contamination of the infant formula or getting formula on the user's hand. Additionally, the scoop portion 142 is sized to permit receiving a measured amount of infant formula (or other material) for insertion into a baby bottle. For example, two scoops of infant formula of a 9.0 gram scoop will be sufficient for making a two (2) fluid ounce bottle of infant formula. Additionally, as noted above, the amount of infant formula in scoop 142 may be leveled at edge 110 of docking station 36. Referring to FIGS. 11 and 25 the outside dimensions of the scoop 142 may be sized to allow scooping out last remaining bits of infant formula in the container. Referring to FIG. 11, the scoop 142 may fit generally in region "X" for removal of the infant formula. Referring to FIG. 25, the scoop 142 has complementary dimensions to the corner areas formed by the junctions of the front and side walls and the back and side walls, thereby allowing the scoop portion to fit flush in these corner areas to remove the last amounts of infant formula.

Lid 28 includes a vertical outer wall 150 with a ledge 152 and an inner vertical wall 154. Wall 154 extends inwardly and upwardly to a juncture 156 providing at the top of the lid a generally flat rectangular track 158 having adjacent thereto slightly recessed portions 160. The recessed portions 160 extend upwardly meeting at an oval track 162 which extends upwardly to provide an oval ridge 164. The oval ridge 164 provides for an aesthetically pleasing appearance. It is also sized to mate with bottom 58 for stacking one or more of the canisters 20, wherein oval ridge 164 mates with recess 70 and the outer edge of track 158 mates with the inner edge of base 64. However, shapes other than oval may be used without departing from the scope of the invention.

The inner portion of lid 28 includes a groove 159 formed by walls 150 and 154 and ledge 152. As seen in FIG. 3, this groove allows for the lid to close and seal on the wall 84 and ledge 82 of base 26. Also, wall 84 of this closure means of the canister may prevent the spilling of infant formula outside of the closure and any formula will fall back into the container through opening 42 of the base 26.

Latch 40 includes a downwardly extending member 160 from lid 28 having an aperture 162. Latch 160 engages member 164 of the base 26 which includes a recessed area 166 in the wall 80 and adjacent shoulder portions 168. Recessed area 166 in wall 80 provides for a substantially smooth surface and a pleasing appearance.

Canister 20 may include multiple means for determining whether the canister has been tampered with. For example, as shown in FIG. 1, the canister may include a seal 170 spanning between the base 26 and lid 28. If the seal is broken, there is evidence of possible tampering. Additionally, if the flanges 144, 146 and 148 holding utensil 34 are broken, this further may indicate that the canister has been tampered with. Similarly, if the sealable material 32 is cut, slit or otherwise open, including by means of ring tab 30, the infant formula or other material may have been tampered with.

Referring to FIG. 4, the canister 20 may also include an electronic article surveillance ("EAS") device 200 located in recess 202 of container 22. The EAS device may be any known device such as a radio frequency EAS device or an acousto-magnetic EAS device. Such devices will deter or prevent theft of the infant formula canister as known to those skilled in the art. Similarly, a more advanced EAS device may be used which will monitor inventory, such as known RFID devices. The EAS device 200 is attached by any known means in recess 202, such as by an adhesive. The infant formula canister will be covered by a label 204 which will include trademark(s), instructions for the infant formula and the like. In a preferred embodiment, the label will include an adhesive 208 for adhering the label to the canister. However, the adhesive 208 on the label 204 may not be applied to area 210 in order that the label will not adhere to recess 202 and EAS device 200. This will preclude the label from adhering to the EAS device 200 thereby indicating to the consumer the presence of the recess 202 and EAS device 200. It will also maintain the label uniformly across the container 22, thereby maintaining an aesthetically pleasing appearance.

Figure 15:
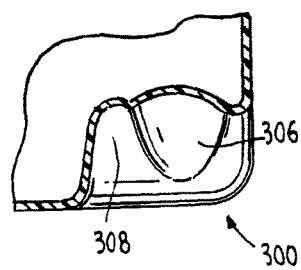
FIG. 15 is a partial cross-sectional view taken along line 15-15 of FIG. 14.
Figure 14:
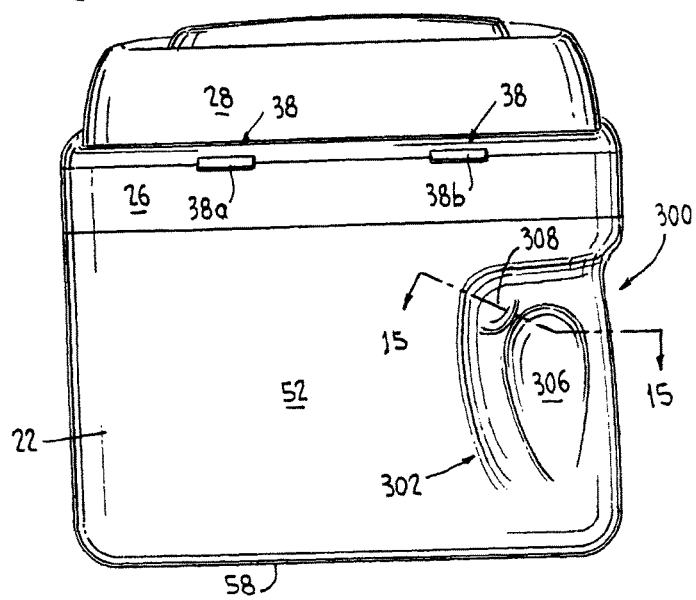
FIG. 14 is a rear elevational view of the canister of FIG. 13.
Figure 30:
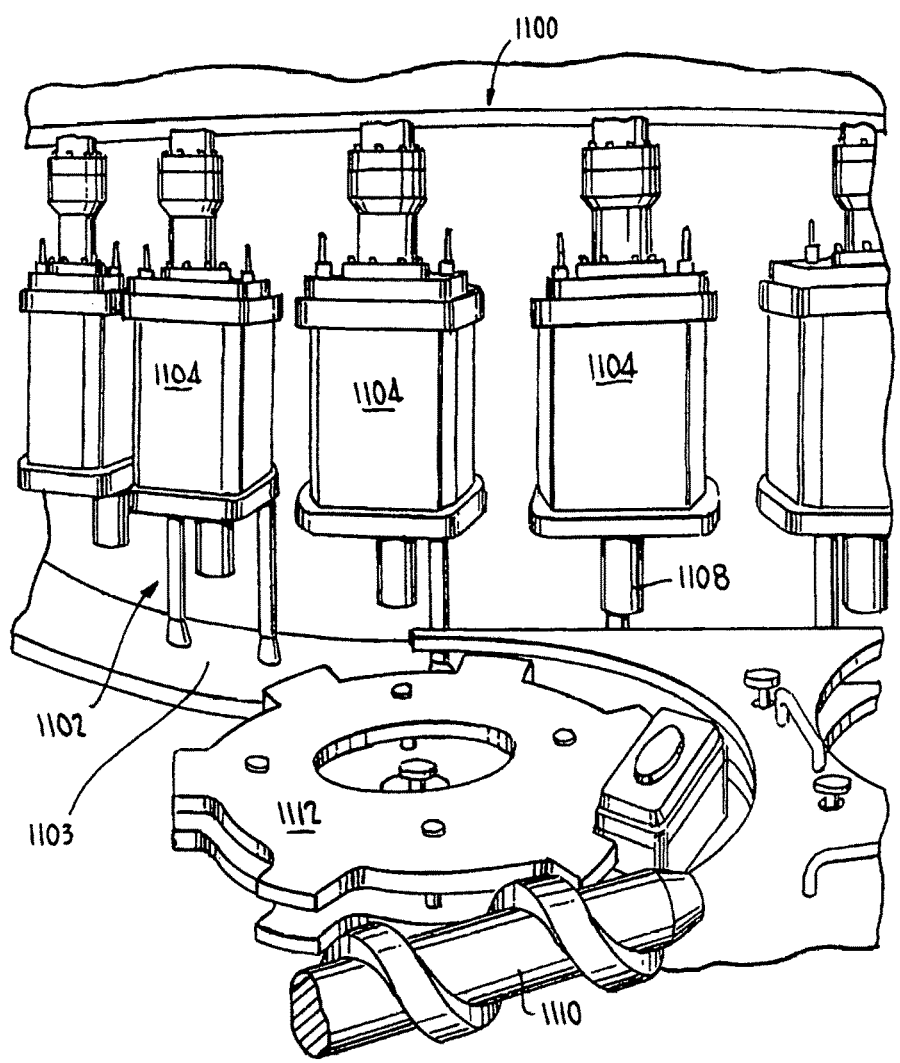
FIG. 30 is a partial perspective view of the apparatus for in-line leak detection of the canister.

Referring to FIGS. 13-16, there is a disclosed second embodiment of the canister of the invention. This embodiment is substantially the same as the first embodiment as indicated by the like reference numbers with the exception that container 22 includes gripping means 300 for gripping the container. The gripping means 300 are located at an end of container 22 and include finger grips 302 and 304 on each side of the container. The finger grips 302 and 304 are the same and will be described hereafter with respect to grip 302. When the canister is made for infant formula, the gripping means may be sized to fit a female's hand as they are generally the primary caregivers for infants. Referring now to FIGS. 14-16, finger grip 302 includes two recesses 306 and 308. Recess 306 is larger than recess 308 and is generally tear-shaped. Recess 306 is for initially gripping the canister and holding the canister. The second recess 308 is smaller and is for receiving a finger or thumb for more tightly gripping the canister.

Alternative embodiments of the docking station are shown in FIGS. 17, 18 and 19. Referring to FIG. 17, the docking station 400 may include a protruding portion 402 configured to mate with the interior of scoop 142 of utensil 34.

Referring to FIG. 18, docking station 500 may include a raised annular portion 502 having an aperture 504 sized to fit and hold the underside of scoop 142.

Referring to FIG. 19, docking station 600 comprises an aperture 602 in the triangular portion 100 for receiving the utensil 34 at the topside of scoop 142.

Referring to FIGS. 20-24, there is disclosed a third embodiment of the canister of the invention, canister 720. This embodiment is substantially similar to the first embodiment as indicated by like reference numbers with the exception that the container 722 is constructed differently at the rim for connecting with the cover 24, and the means for connecting container 722 and cover 24 is different from the first and second embodiments. This embodiment uses induction sealing means for connecting the container 722 and cover 24. Specifically, container 722 includes an upper portion 800 having a rim 810, ribs 820 along front wall 50 and back wall 52 and grooves 830 in the upper portion 800 of the side walls 54 and 56. Container 722 front wall 50, back wall 52 and side walls 54 and 56 have a shoulder 802 joining rim 810 with an inwardly and upwardly extending wall 804. Ribs 820 are spaced apart with recesses 822 therebetween. Grooves 830 are separated by a support rib 832. The top of rim 810 includes a generally flat portion 840 for engagement with cover 24. Flat portion 840 may be in the range of 0.060 inches to 0.100 inches, and preferably 0.080 inches. Ribs 820 and grooves 830 provide rigidity and support strength to the container 722. Cover 24 is attached to container 722 by induction sealing. The foil material 32 is an induction sealing foil, for example, Coflex Laminate MDPE/0.001/100CPP manufactured by Coflex Packaging, Inc., Quebec, Canada, which is attached to the underside of base 26 of cover 24. Cover 24 is sealed to container 722 by induction sealing. In this process, cover 24 is placed on container 722 and pressed onto the container at a cylinder (a 32 mm diameter cylinder) pressure set on the machine in the range of about 40 to 50 lbs. per square inch, and preferably 45 lbs. per square inch. (The actual sealing pressure (lbs.) measured at the face seal is thus force (psi) multiplied by the cross sectional area (sq. inches) of the container land.) The upper portion 800 provides strength to container 722 to absorb such pressure without deforming the filled container.

Referring to FIG. 24, induction sealing foil material 32 is sealed to flat portion 840 providing a strong seal to secure cover 24 to container 722.

Referring to FIGS. 26-28, there is disclosed an apparatus and method for transporting the covers 24 during the process of manufacture. Specifically, covers 24 are first made in one process, and container 22 or 722 is first made in another process. Thereafter, the cover 24 is attached to container 22 or 722. Accordingly, in one process, the container 22 or 722 and covers 24 are transported to the manufacturing facility. The covers 24 are transported on pallets with a number of layers of covers, e.g. 50 layers with 72 covers per layer. During transport of the covers, it has been proposed to separate the covers by a slip sheet. This slip sheet is usually made of material such as polypropylene and is a unitary sheet. However, as seen above, cover 24 includes base 26 and lid 28 having the utensil 34 held in place. During transport, if too much pressure is applied to the top of lid 28, the pressure may cause the utensil 34 to push downward and damage or tear the foil material 32. In order to avoid this problem, it has been discovered that by using slip sheets having openings sized to surround the lid area 164 of the cover, there is no such pressure on the lid, thereby preventing the possibility of damage to the foil 32 of the cover.

Referring again to FIGS. 26-28, there is shown the pertinent aspects of the invention. As seen in these Figures, there are a plurality of covers 24 stacked on a pallet to be placed onto the assembly line of the manufacturing process. The covers 24 are removed from the pallet and placed onto the assembly line by a vacuum suction mechanism 1000. The slip sheets are thereafter removed and the next layer of covers 24 are available for removal from the pallet and placing on the assembly line. As seen in these Figures, the slip sheet 1002 includes openings 1004 sized to fit around oval ridge 164 of cover 24. This prevents excessive pressure on the top of the lid which may compress the lid causing the utensil 34 to damage foil 32.

The present invention further provides a canister which can withstand substantial pressure during the manufacture process, and it is believed greater than the known infant formula canisters. Specifically, when attaching the cover 24 to the container 722 as referenced above with respect to the canister of FIGS. 20-24, pressure is applied to the top of the cover 24 during the induction sealing process. Due to the structure of the cover 24 and container 722, substantial pressure may be applied to the cover, e.g. at least 40 psi. This allows for a good seal for the cover to the container.

Additionally, the canister shown in FIGS. 20-24 have been found to withstand higher internal pressure without rupturing the foil seal attached to the container or rupturing the foil. This provides for a sturdier canister during transport, including when changes in elevation occur in transport.

As stated above, the container 22 and cover 24 are made by separate manufacturing processes. In a preferred embodiment the container is made of polyethylene and the cover is made of polypropylene. The container and cover are usually opaque and may be different colors, e.g. the container white and the cover blue. In a preferred embodiment, the cover and utensil, which are made in the same process, are the same color and opaque. However, it has been found useful to make the cover opaque and the utensil transparent. This allows the caregiver to see the amount of infant formula in the scoop portion of the utensil.

Operation

In operation, the canister is used as follows. First, tamper resistant seal 170 is either removed or broken. Then latch 40 is opened as shown in FIG. 4 exposing utensil 34 and sealing material 32. Utensil 34 is removed by breaking frangible members 144, 146 and 148 and the utensil is removed from the canister. Next, ring 120 is lifted up and teeth 128 engage and cut sealing material 32 to start the removal thereof. Ring tab 120 is then pulled along the periphery of the container and perforations 130 are broken allowing removal of all of the sealing material 32 thereby providing an opening 42 in base 26 and exposing the infant formula or other material C. Ring 120 and the corresponding sealing material 32 may then be thrown away. Utensil 34 may be used to scoop out a measured amount of infant formula or other material. Edge 110 of docking station 36 may be used to level the amount of formula in scoop 142. Once the infant formula is dispensed, utensil 34 may be placed in docking station 36 as shown, for example, in FIG. 12. The canister may then be closed with latch 40 maintaining the canister in a closed position to avoid spillage of the infant formula.

Manufacturing Process and in-Line Sterilization of Canister Cover

As stated above, the canister invention includes container 22 or 722 and cover 24. In one preferred manufacturing process containers 22 or 722 and cover 24 are made and transported to the manufacturing facility; the containers 22 or 722 are filled with infant formula as described above; and the cover 24 is attached to the container. The cover 24 is transported to the manufacturing facility complete and in a closed position, the interior of the cover having been sterilized during the manufacturing process. However, the underside of the cover having foil 32 is subject to exposure to the elements during transport and must be sterile prior to attaching the cover 24 to the container 22 or 722, the foil being adjacent to the infant formula and subject to contact with the infant formula.

Referring to FIG. 29, there is disclosed a perspective view of part of the in-line manufacture of the canister wherein the underside of the cover is sterilized. The canister cover 24 is shown closed as received from the manufacturer. The manufacturer has already treated the inside of the cover with UV treatment to sterilize the interior of the cover. The cover is closed at their facility and, therefore, the integrity and cleanliness of that inside is not violated. However, the product contact surface is exposed. Thus, in shipping there may be environmental contamination. Therefore, during the in-line manufacture, the underneath of the cover is subject to UV sterilization before its put on the container 22 or 722. In this process, the cover 24 comes into the UV sterilization tunnel 2000 by conveyor 2002. The cover rides on gripper belts 2004 such that the cover is held and moved by the gripper belts. The cover is supported by two rails 2003 extending longitudinally through the sterilization tunnel. There are UV bulbs underneath at 2006 shining up. The cover is, therefore, subject to UV sterilization of the foil face 32 that will be in product contact. The cover 24 is thereafter transported to a station having the container 22 or 722 (now filled with infant formula) and the cover 24 is attached to the container as described above.

Manufacturing Process and in-Line Detection of Leaks in the Canisters

As also stated above, the canister invention includes container 22 or 722 and a cover 24. In one preferred manufacturing process, containers 22 or 722 and cover 24 are made and transported to the manufacturing facility; the containers 22 or 722 are filled with infant formula as described above; and the cover 24 is attached to the container, e.g. by induction sealing as referenced above for canister 720. The infant formula will usually have a guaranteed shelf-life, e.g. of 24 months. If there are leaks in the canister, the air allowed into the canister may affect the shelf-life of the infant formula. In the past, completed infant formula canisters were randomly pulled from the manufacturing line and tested for leaks in the canister, e.g. in a water-vacuum test chamber. The present invention is directed to an apparatus and method wherein each canister is tested for leaks in-line during the manufacturing process. This provides for total quality assurance testing of each canister before it leaves the manufacturing facility. If a leak is found in the canister, the canister is rejected; the infant formula sent to be re-worked and then used in subsequent filling; and the canister discarded.

FIGS. 30-34 show a preferred embodiment of the apparatus and method for in-line vacuum leak detection of the canister 720 as shown in FIGS. 20-24. The apparatus 1100 is manufactured by Wilco AG, of Switzerland, and has been modified to provide for the leak detection on the canister invention. The apparatus 1100 includes a plurality of stations for the in-line leak detection. Referring to station 1102, the station includes a flat surface 1103 for receiving the canister; a shroud 1104; inside the shroud is a block 1106 which is constructed and arranged to accommodate different height canisters 720; and a plunger 1108. The shroud 1104 moves vertically and over canister 720, therefore, creating a vacuum chamber for leak detection as discussed hereafter. Plunger 1108 serves to (1) hold the canister 720 in place prior to shroud 1104 moving downward over the canister, and (2) to aid in the evacuation of air in the sealed cover 24 as described in greater detail hereafter.

Figure 31:
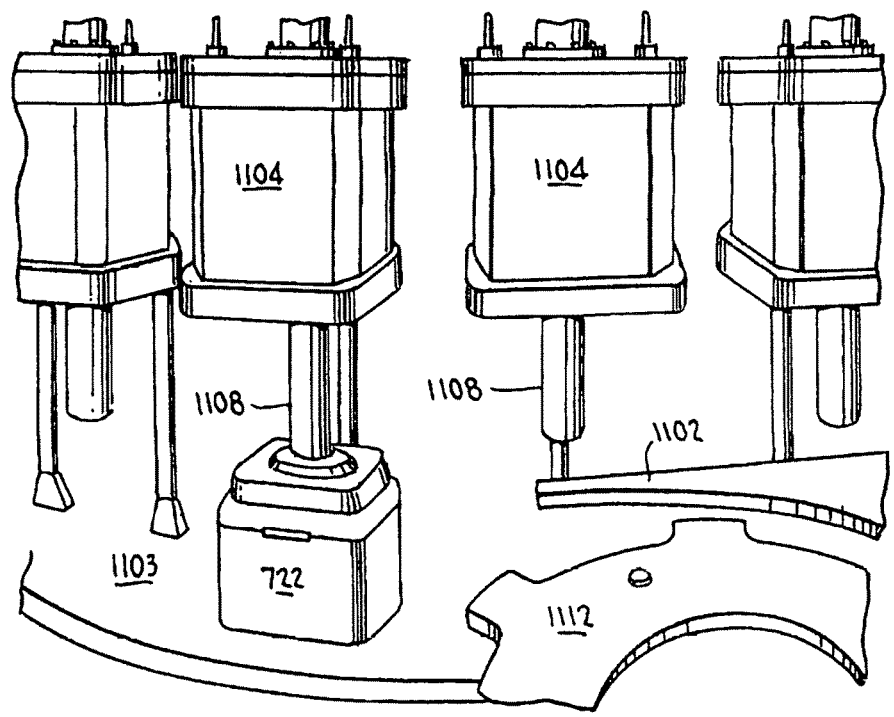
FIG. 31 is a close-up perspective view of one station of the apparatus with a canister for in-line leak detection of the canister.
Figure 32:
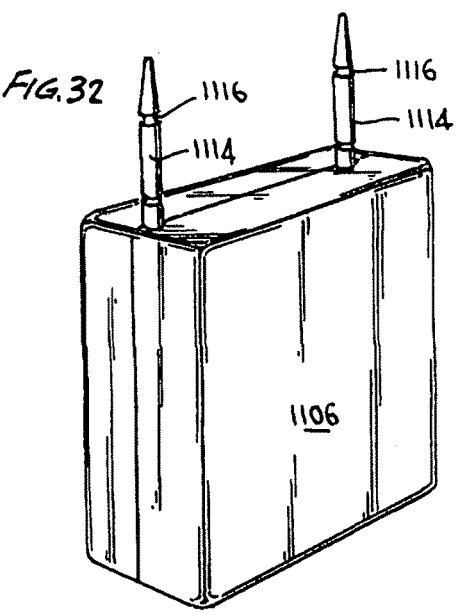
FIG. 32 shows the removable block which vary in size thereby allowing different size canisters to be vacuum leak tested within the same shroud.

In operation, the canister 720 comes in through the screw 1110 and enters the star wheel 1112 (only one canister being shown in the star wheel for purposes of illustration). From the star wheel, the canisters are then indexed under each one of the station 1102. The canister 720 is indexed under a shroud 1104, as shown in FIG. 31. The plunger 1108 comes down to hold the canister in position such that centrifugal force does not move the canister. The shroud 1104 then comes down and seals over the canister. Once the shroud comes down, the vacuum chamber is sealed. Then a predetermined amount of air is pulled out of the chamber. A predetermined vacuum set point is established to determine that the canister is not leaking. If the canister is leaking, the predetermined vacuum set point is not achieved and the canister has a large or gross leak. If the canister is not leaking, the canister has achieved the set point. Next, the process goes into an equalization phase, namely, there is a steady-state environment, and it is determined what the vacuum level is and then the process looks for vacuum decay. When there is a small change in the vacuum level over time, this indicates a small or micro leak somewhere in the canister.

In order for this vacuum test system to function properly, the space underneath the lid 28 of cover 24 must be evacuated of any air. If the air is not completely evacuated, the air will slowly leak out and it will show up as a small leak during the vacuum decay test phase, thereby rendering the leak detection test of no value. The evacuation of the air is achieved based on the design of the edge 84 and groove 159 of the cover 24 for sealing the canister when the plunger 1108 comes down and pushes on the top of lid 28 as shown in FIG. 31. There is a small amount of deflection which causes sufficient movement of the lid 28 to facilitate the releasing of any air inside the cover 24.

Figure 31A:
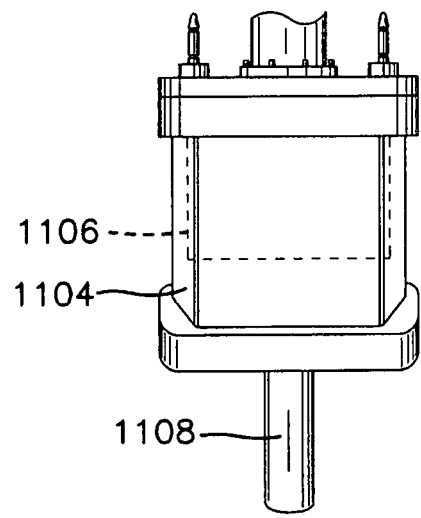
FIG. 31A is a close up view of the shroud showing the block inside the shroud in dashed lines.
Figure 31B:
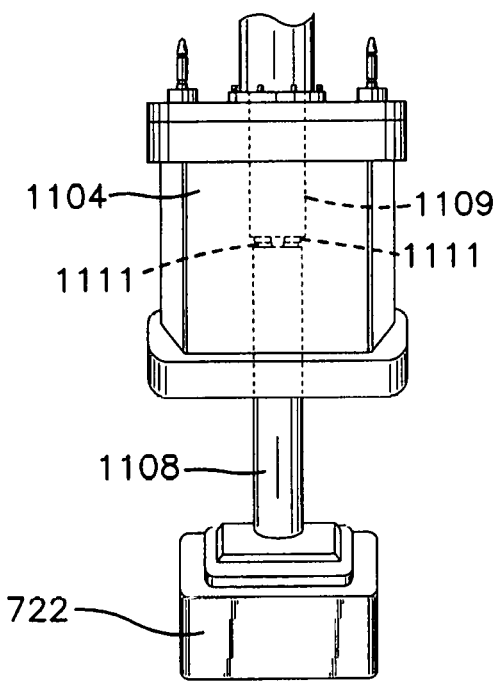
FIG. 31B is a close up view showing the push rod and the plunger in dashed lines inside the shroud.

As noted above, the containers 22 and 722 may be made in different sizes to accommodate different amounts of infant formula, e.g. 20 ounces, 35 ounces, and 50 ounces. There are two change parts in the apparatus requiring change to accommodate each size of container. First, the plunger will vary in height depending on the size of the container. The plunger is easily changed by the use of rare earth magnets 1111 to attach the plunger to the push rod 1109 of the apparatus. Referring to FIG. 31B, in a preferred embodiment, two magnets are used. The magnets attract and hold the plunger in place and when the plunger is twisted, the magnetic poles repel and push the plunger down so that it is easy to remove. Referring to FIG. 31A, the second part requiring change is this block 1106 inside shroud 1104 which fills the vacant space within the shroud caused by the varying height of the canister. This change-over has been made tool-less and simple for the operator to change. Instead of using any nuts and bolts or the like, the apparatus uses a spring loaded detent clamp system which clamps on grooves 1116 of pins 1114 and allows for ease of release of the block; dropping the block out of the shroud; inserting the new block and putting the block back in and locking the block in place by the detent clamp engaging grooves 1116.

Figure 33:
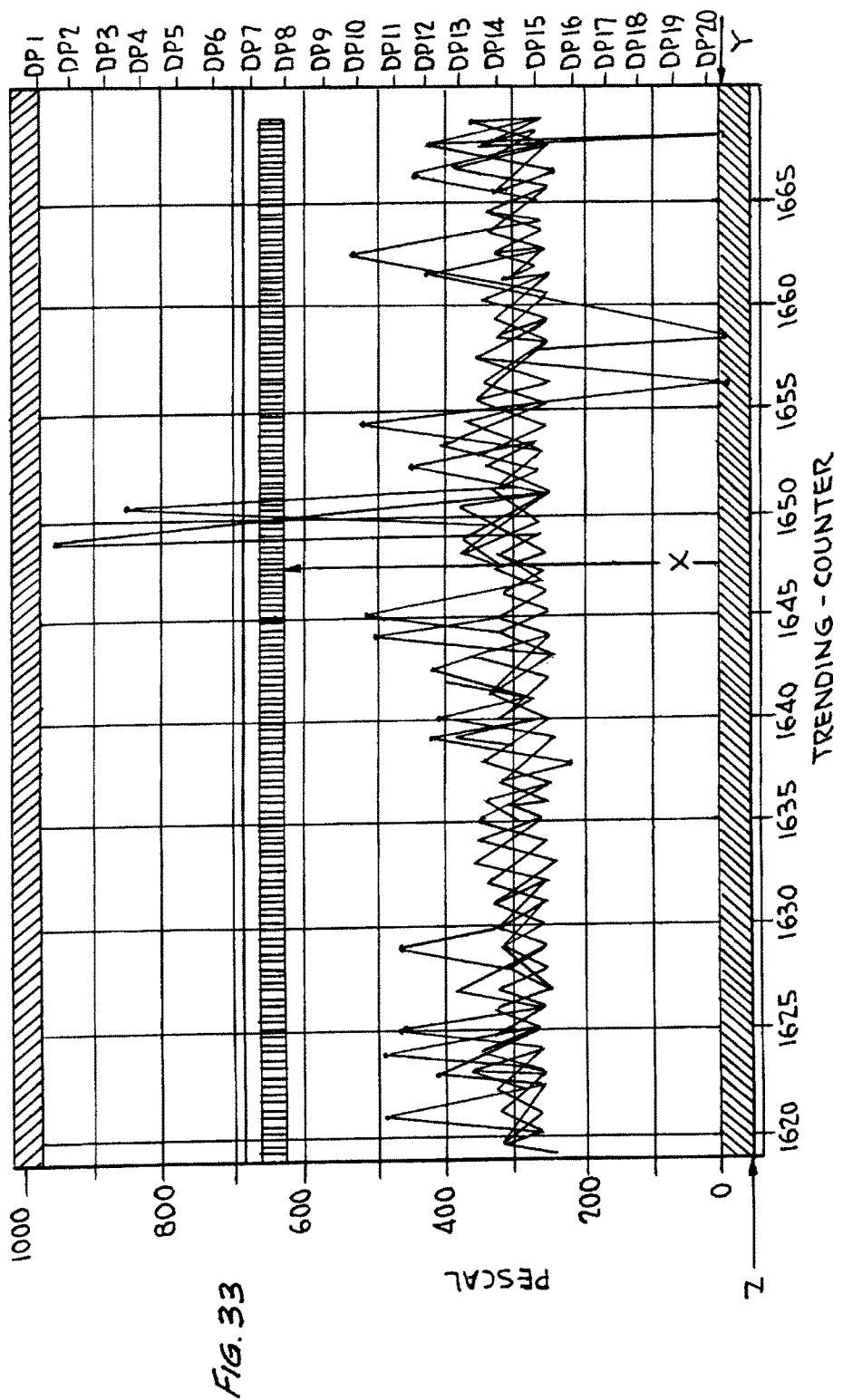
FIG. 33 is a view of the computer screen showing the results of the in-line leak detection.
Figure 34:
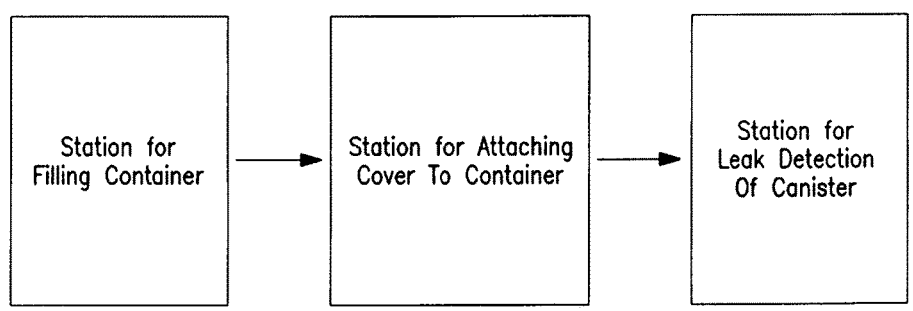
FIG. 34 is a block diagram showing certain of the stations of the apparatus.

Referring to FIG. 33, there is shown a trending display generated by a software component of a processing computer monitoring the leak detection. If a canister is considered good, it will be within this bandwidth "X." If a reading is above this bandwidth "X" during the vacuum decay phase, this indicates a small leak. If there is a reading below line "Y" and in band "Z," then there is a gross leak which will be detected during the initial vacuum pull down phase. Anything within bandwidth "X" is noise and considered an acceptable non-leaking canister. When a leak is detected, the processing computer through a software component causes the apparatus to remove the canister from the production line.

The exemplary embodiments herein disclosed are not intended to be exhaustive or to unnecessarily limit the scope of the invention. The exemplary embodiments were chosen and described in order to explain the principles of the present invention so that others skilled in the art may practice the invention. As will be apparent to one skilled in the art, various modifications can be made within the scope of the aforesaid description. Such modifications being within the ability of one skilled in the art form a part of the present invention.

It is claimed:

1. An apparatus for manufacturing a canister having a cover and container, the cover having a base and a lid and a foil attached to the base of the cover, the apparatus comprising
    a station for filling the container with a selected content,
    a station for attaching the cover to the container,
    a station for leak detection of the canister comprising (a) a flat surface for receiving the canister, (b) a shroud having a block within the shroud for mating with the canister, (c) a movable plunger for engaging the canister, and (d) a processing computer,
    wherein said plunger is adapted for downward movement and engagement with the cover of said canister to hold said canister in place on said flat surface and push down on a top surface of the lid of the cover to provide sufficient movement of the lid and thereby evacuation of any air between said base of the cover and said lid, said shroud is adapted to move down and seat on said flat surface and surround said canister to form a vacuum chamber and to allow a predetermined amount of air to be pulled out of said vacuum chamber to form a vacuum therein, and said processing computer is adapted to interface with said apparatus to generate data sufficient to indicate whether there is a leak in said canister.

2. The apparatus of claim 1 further comprising means to remove and replace said plunger with a different size plunger.

3. The apparatus of claim 2 wherein said means to remove and replace said plunger comprises one or more magnets.

4. The apparatus of claim 1 further comprising means to remove and replace said block with a different size block.

5. The apparatus of claim 4 wherein said means to remove and replace said block comprises one or more pins having grooves for engaging a detent clamp.

6. The apparatus of claim 1 wherein said apparatus further comprises a trending display generated by a software component of said processing computer for monitoring leak detection.

7. The apparatus of claim 6 wherein the processing computer of said apparatus further comprises a software component which causes the apparatus to remove a canister detected having a leak from the production line.

8. The apparatus of claim 1 wherein the apparatus further comprises a station for sterilization of exposed foil on the underside of said cover, said station for sterilization comprising a conveyor for moving said cover to said station, a sterilization tunnel for receiving said cover, means for moving said cover through said tunnel and one or more UV lights for sterilizing said exposed foil.

9. The apparatus of claim 1 comprising a plurality of said stations for leak detection.

10. The apparatus of claim 9 wherein each canister manufactured by said apparatus enters one of said plurality of stations for leak detection.

11. The apparatus of claim 1 wherein said station for leak detection comprises two phases of leak detection.

12. The apparatus of claim 11 wherein a first phase for leak detection detects large leaks and a second phase for leak detection detects small leaks.

13. An apparatus for manufacture of a canister having a cover and a container, said cover comprising a base and a lid and a foil attached to the base of the cover, wherein said apparatus includes a station for sterilization of exposed foil on the underside of the base of said cover, said station for sterilization comprising a conveyor for moving said cover with said exposed foil adjacent to said conveyor to said station, a sterilization tunnel for receiving said cover wherein said sterilization tunnel includes two longitudinal rails for receiving and carrying said cover through said tunnel and adapted to allow sterilization of said exposed foil by a plurality of UV lights, a first gripper belt on one side of said tunnel and a second gripper belt on a second side of said tunnel, said first gripper belt and second gripper belt are each adapted to grip said base of said cover and move said cover through said tunnel without rotating said cover, and a plurality of UV lights at a base of said tunnel for sterilizing said exposed foil.

14. A method for leak detection of a canister, the canister having a cover and a container, the cover having a base and a lid and a foil attached to the base of the cover, comprising steps of
    filling the container with a selected content,
    attaching the cover to the container, providing a station for leak detection of the canister wherein the station comprises (a) a flat surface, (b) a shroud having a block within the shroud, (c) a movable plunger, and (d) a processing computer, receiving the container with the cover thereon on the flat surface, moving said plunger downward to engage the cover of said canister thereby holding said canister in place on said flat surface, pushing down on a top surface of the cover causing sufficient movement of the cover and causing evacuation of any air between said base and said lid of said cover, moving said shroud downward and seating said shroud on said flat surface surrounding said canister to form a vacuum chamber, removing a predetermined amount of air from said vacuum chamber to form a vacuum therein, and generating by said processing computer data sufficient to indicate whether there is a leak in said canister.

* * * * *